US010226560B2

(12) United States Patent
Lanucara

(10) Patent No.: US 10,226,560 B2
(45) Date of Patent: Mar. 12, 2019

(54) DEVICE FOR GENERATING BILATERAL PRESSURE IMPULSES

(71) Applicant: Ubaldo Lanucara, Rome (IT)

(72) Inventor: Ubaldo Lanucara, Rome (IT)

( * ) Notice: Subject to any disclaimer, the term of this patent is extended or adjusted under 35 U.S.C. 154(b) by 37 days.

(21) Appl. No.: 15/507,477

(22) PCT Filed: Aug. 26, 2015

(86) PCT No.: PCT/IT2015/000205
§ 371 (c)(1),
(2) Date: Feb. 28, 2017

(87) PCT Pub. No.: WO2016/030917
PCT Pub. Date: Mar. 3, 2016

(65) Prior Publication Data
US 2017/0281843 A1     Oct. 5, 2017

(30) Foreign Application Priority Data

Aug. 28, 2014   (IT) ............................. RM2014A0484

(51) Int. Cl.
*A61M 1/10*     (2006.01)
*A61M 1/12*     (2006.01)

(52) U.S. Cl.
CPC ........ *A61M 1/1055* (2014.02); *A61M 1/1046* (2013.01); *A61M 1/1049* (2014.02); *A61M 1/125* (2014.02); *A61M 1/12* (2013.01)

(58) Field of Classification Search
CPC .. A61M 1/125; A61M 1/1044; A61M 1/1046; A61M 1/1051; A61M 1/1055
See application file for complete search history.

(56) References Cited

U.S. PATENT DOCUMENTS

| | | |
|---|---|---|
| 4,173,151 A | 11/1979 | Grundy |
| 5,976,184 A | 11/1999 | Buecherl et al. |

FOREIGN PATENT DOCUMENTS

| | | |
|---|---|---|
| DE | 883 540 C | 7/1953 |
| DE | 195 05 512 A1 | 8/1996 |
| EP | 0 754 880 A2 | 1/1997 |
| FR | 1 003 222 A | 3/1952 |

OTHER PUBLICATIONS

International Search Report, dated Mar. 18, 2016, from corresponding PCT application.

*Primary Examiner* — Howie Matthews
(74) *Attorney, Agent, or Firm* — Young & Thompson

(57) ABSTRACT

Disclosed is an electromechanical device generating bilateral pressure impulses, wherein the alternative and specular movement of the homologous cursors (CV, CO), pacing one of the Cartesian axes, exclusively manages mobile cores (NEM) of electromagnets (EM) with planned solicitation, for supplying the necessary mechanical energy for the correct working of operating machines of different kinds, and in particular of a permanent artificial heart.

20 Claims, 13 Drawing Sheets

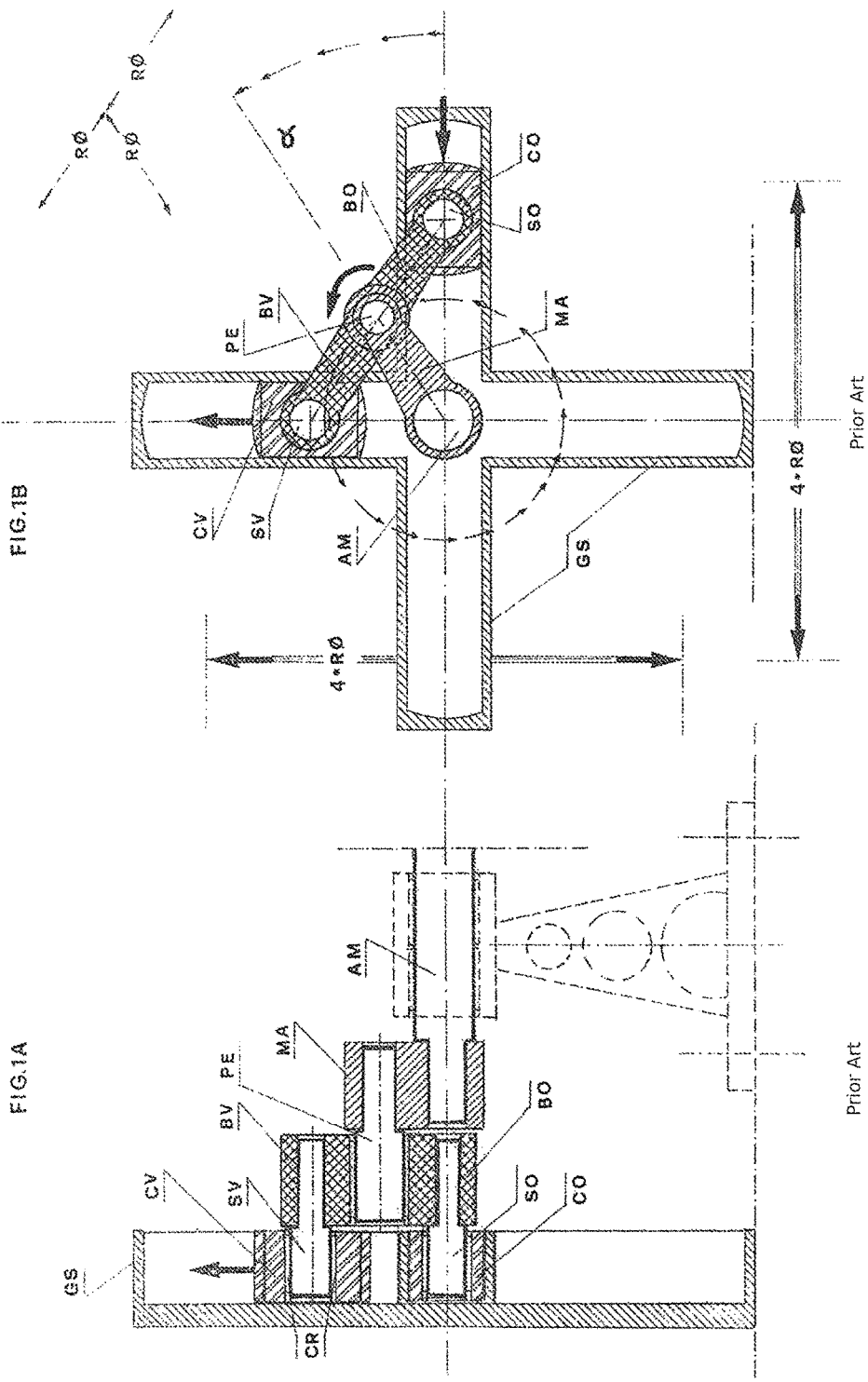

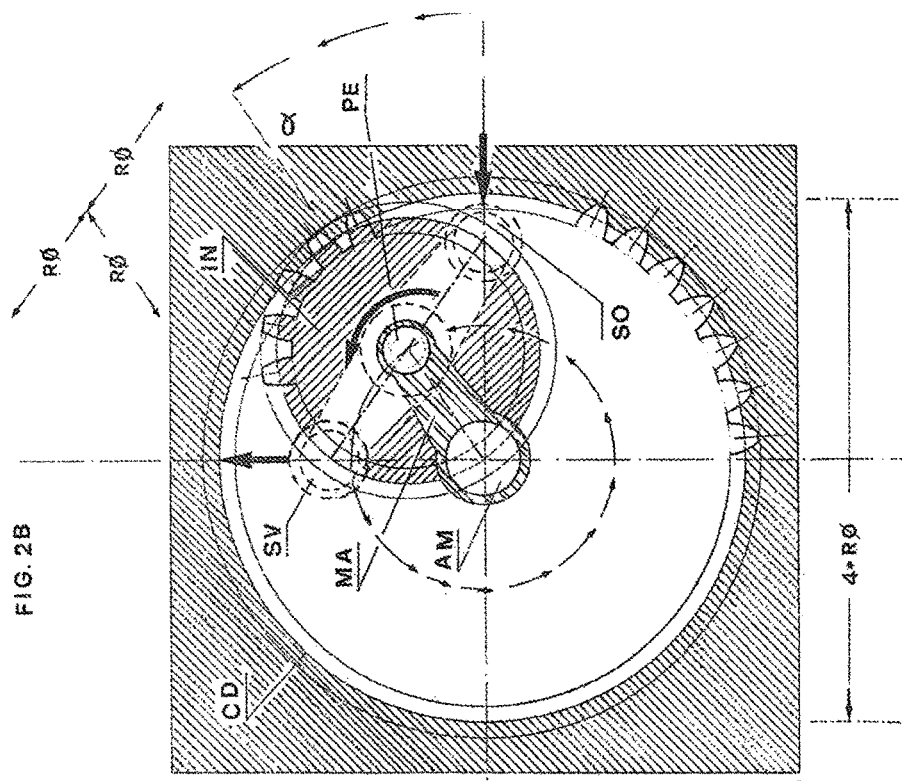
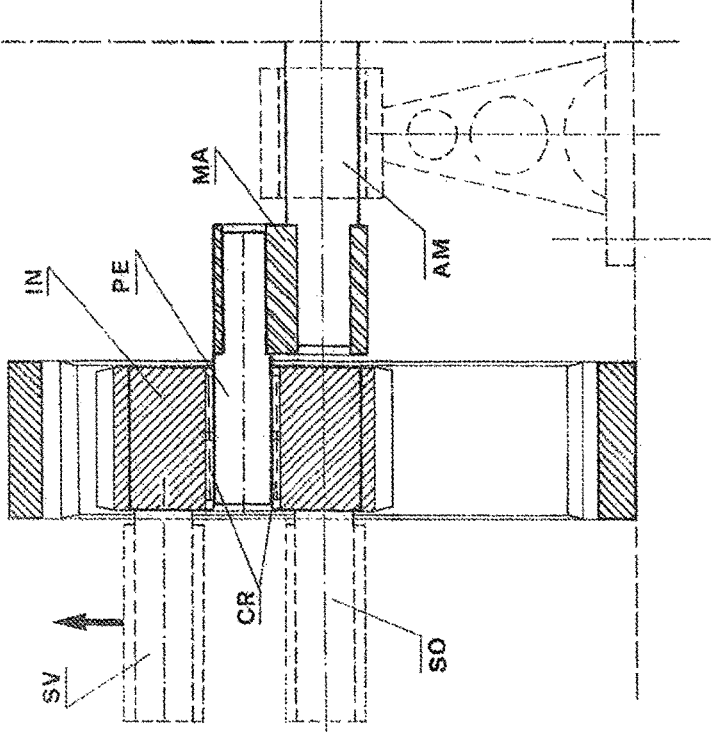

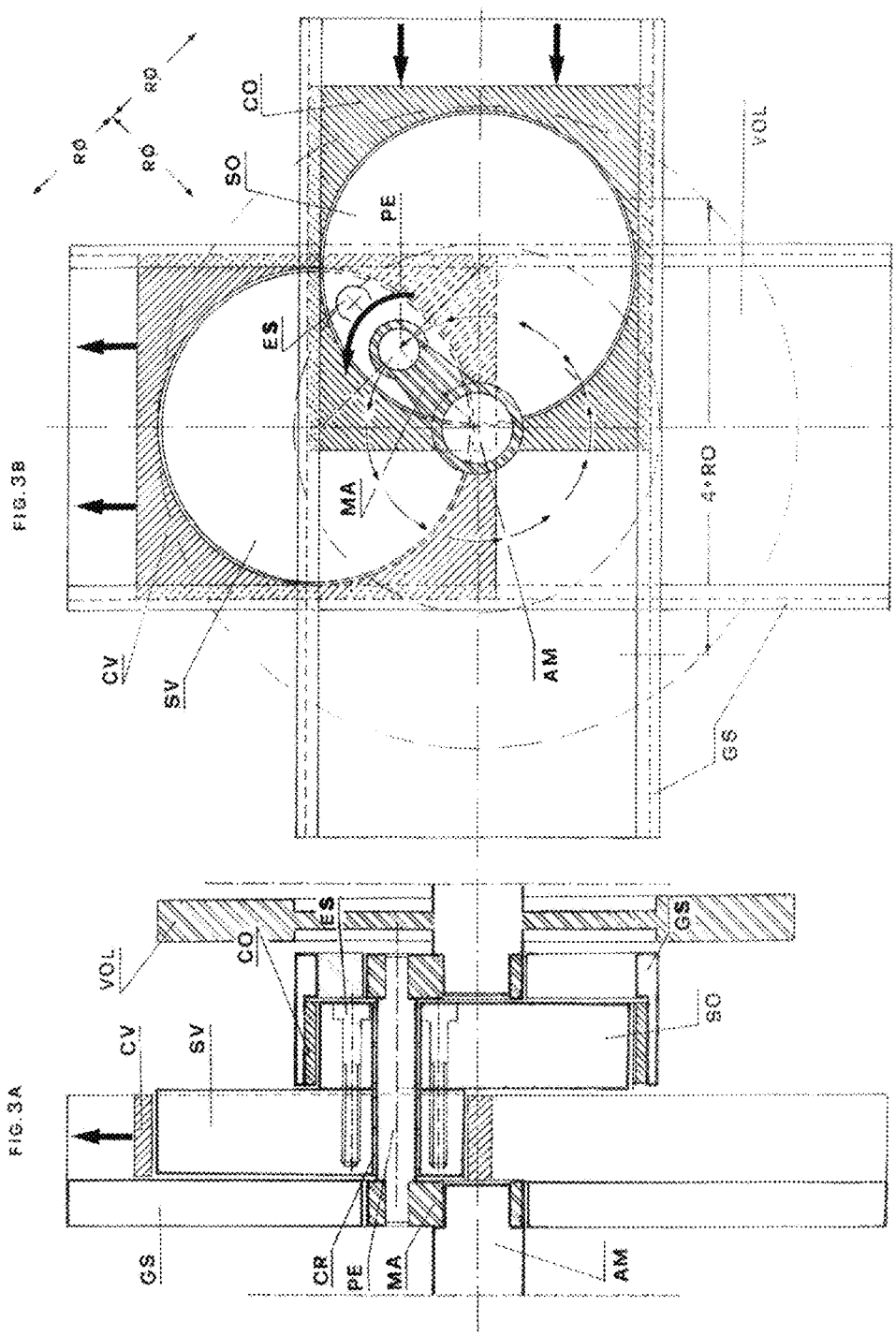

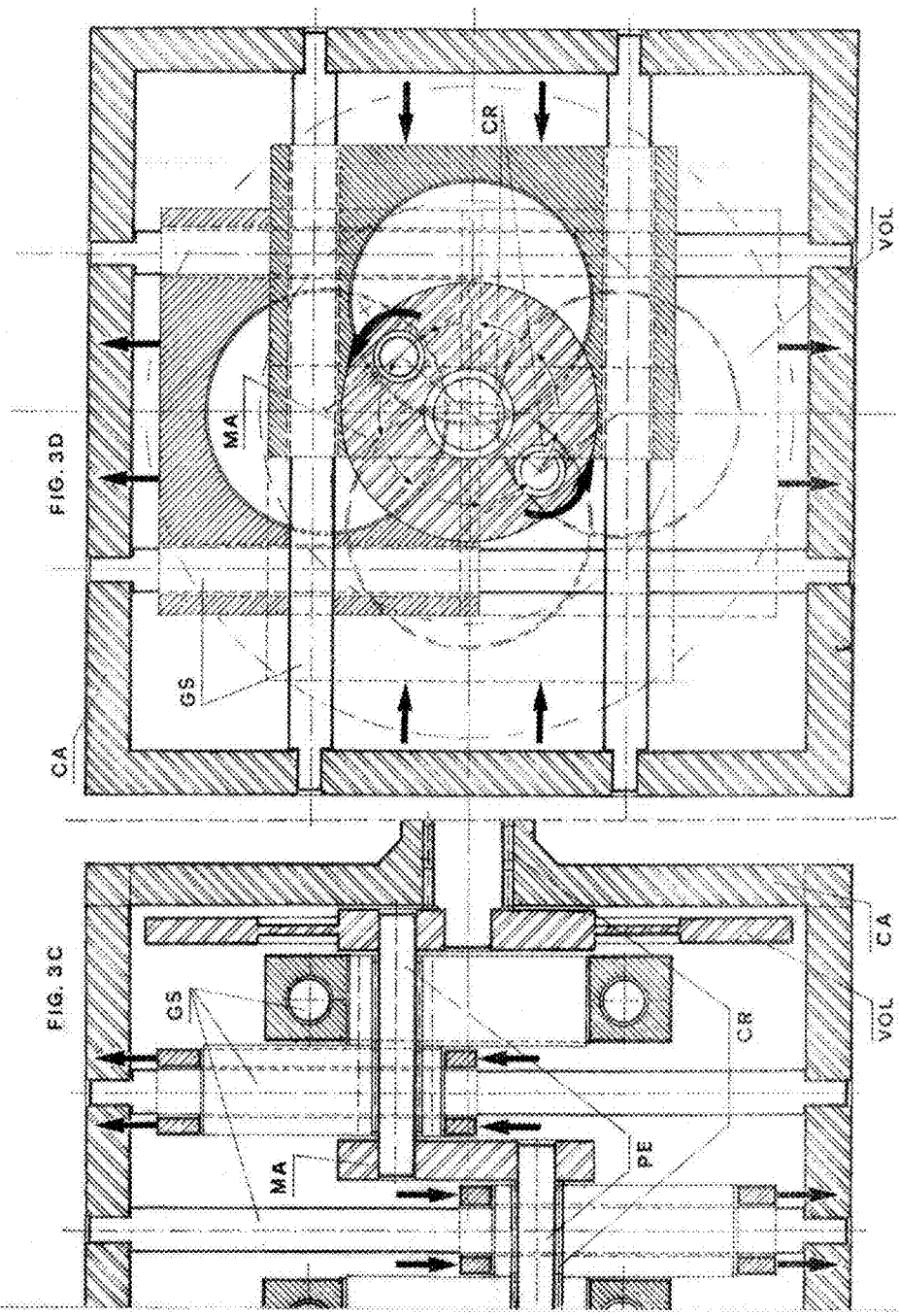

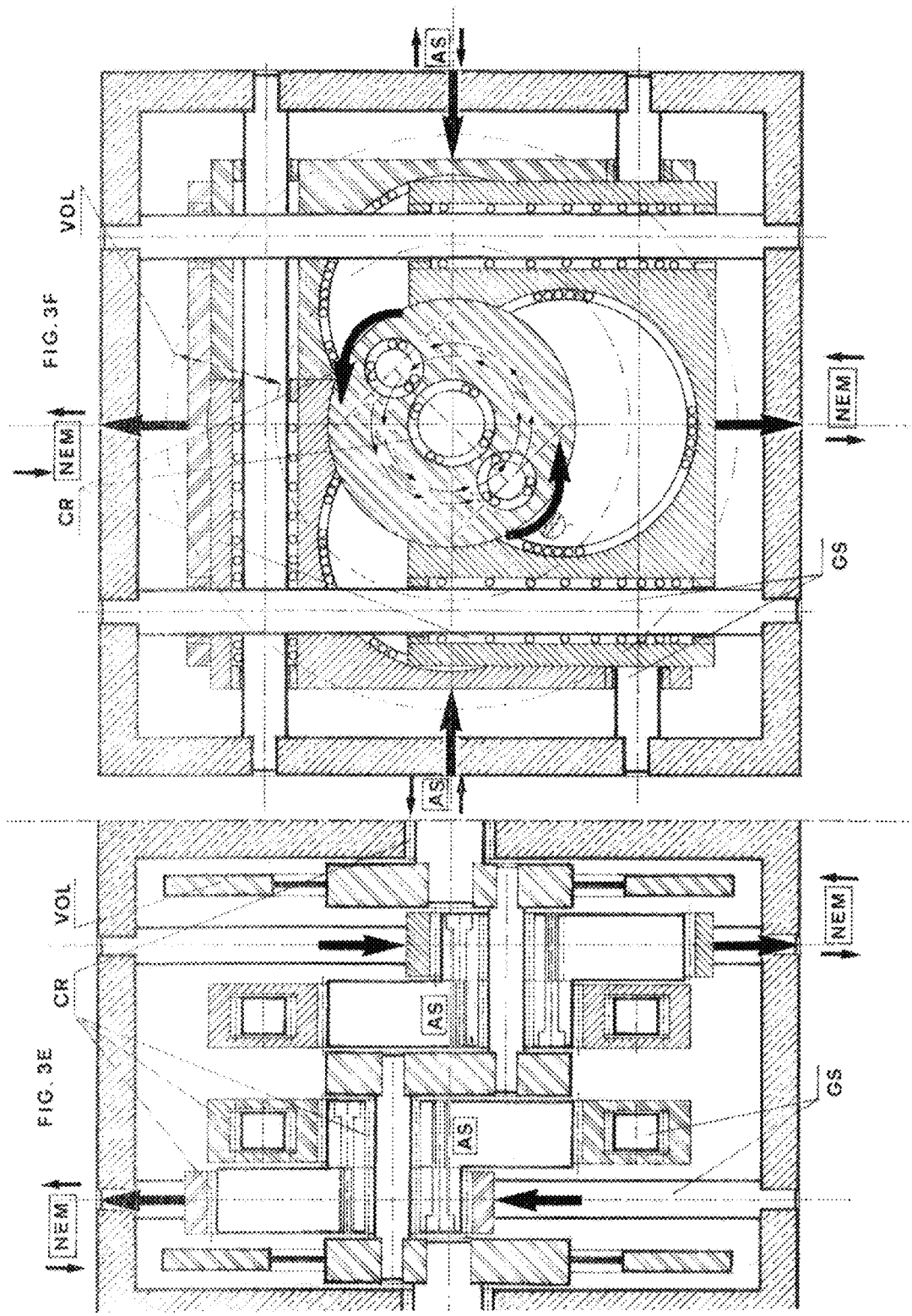

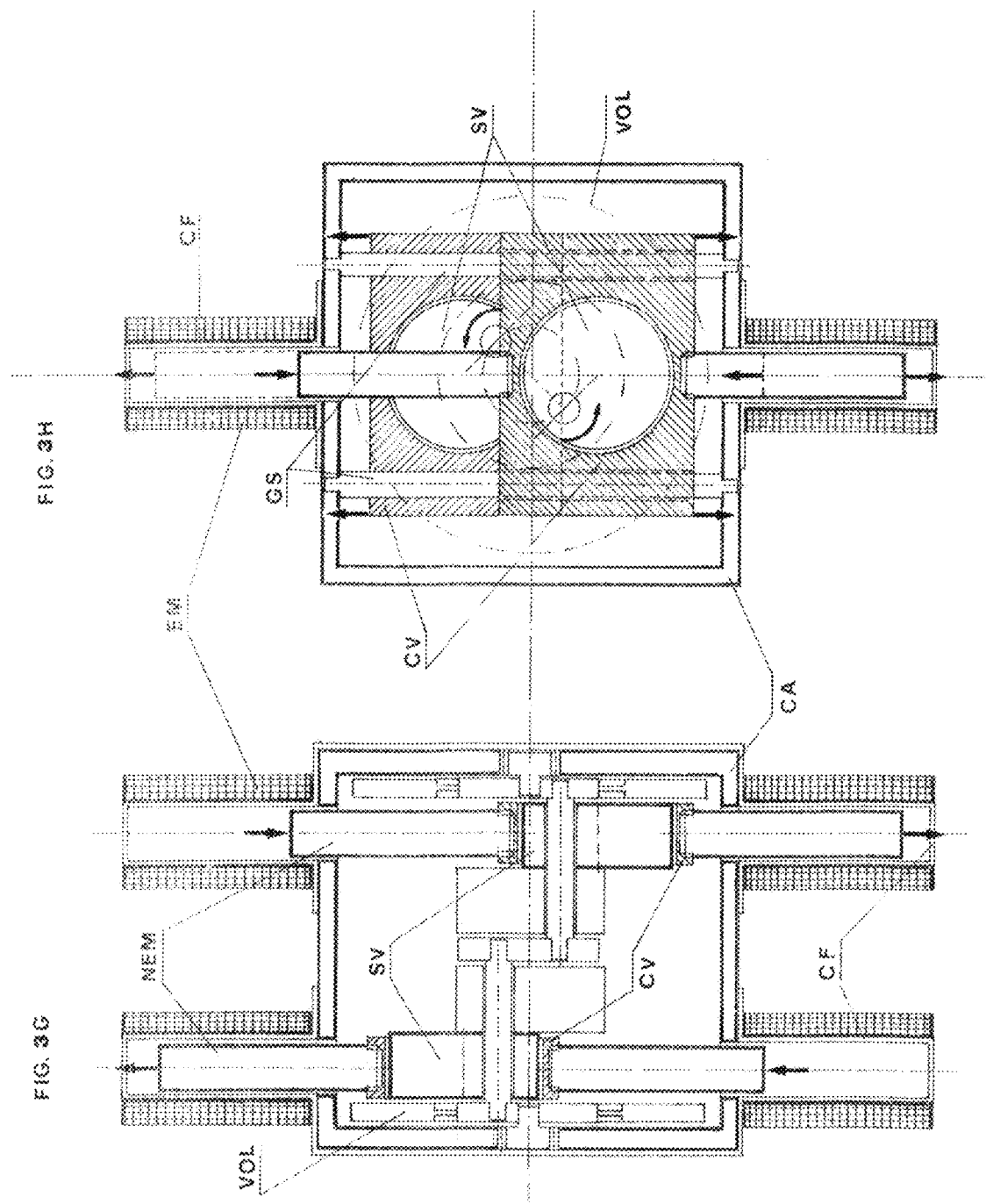

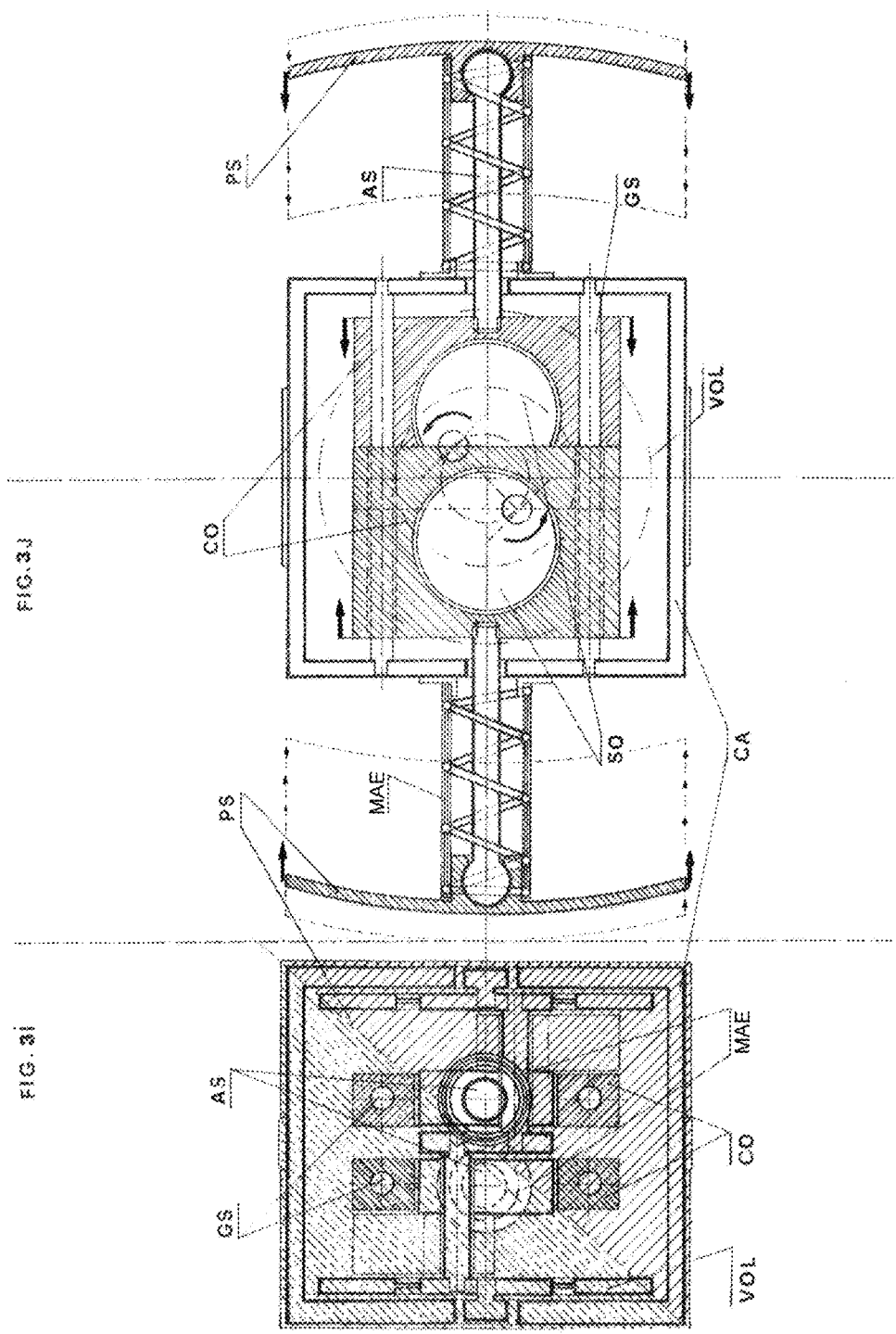

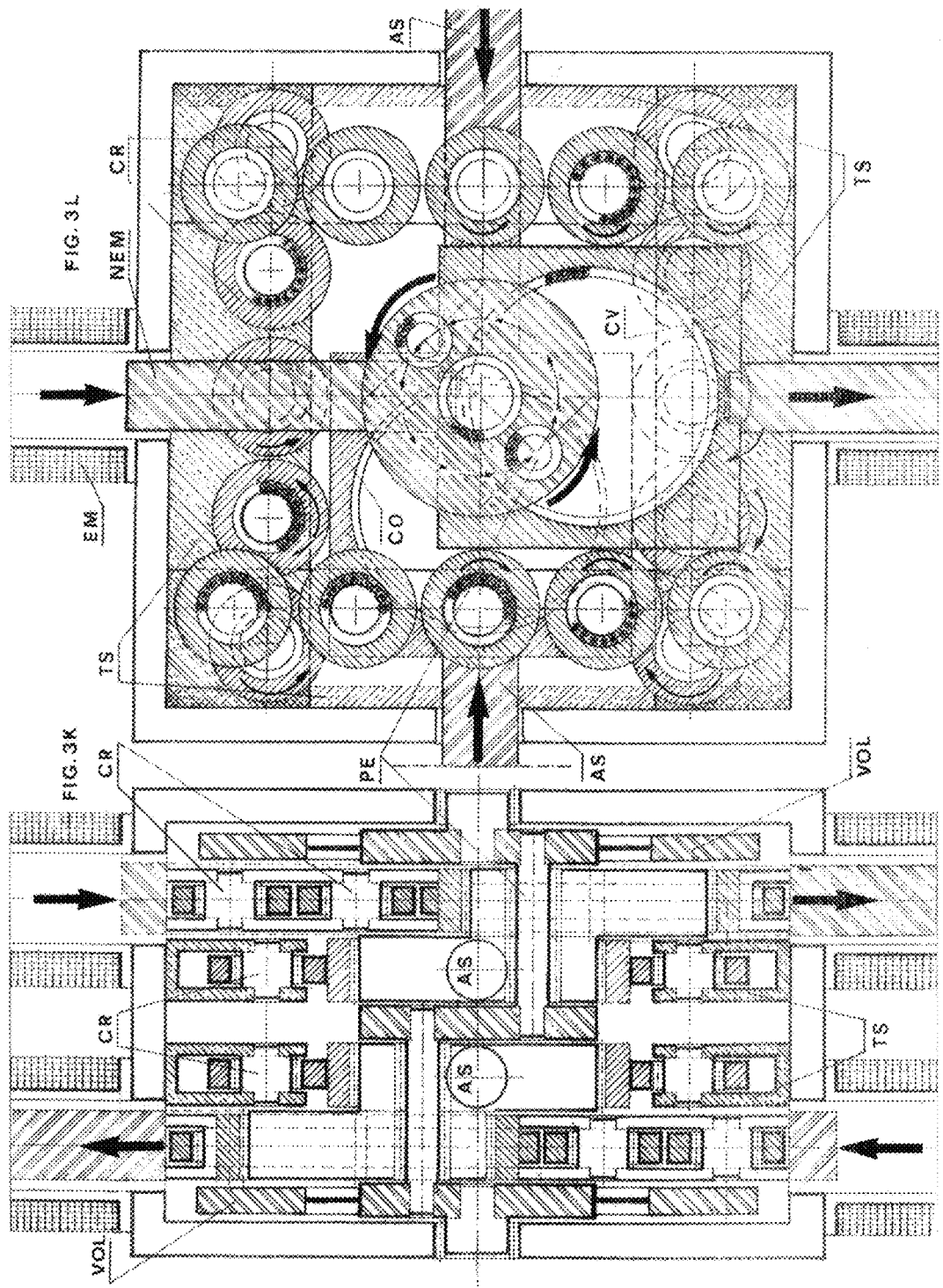

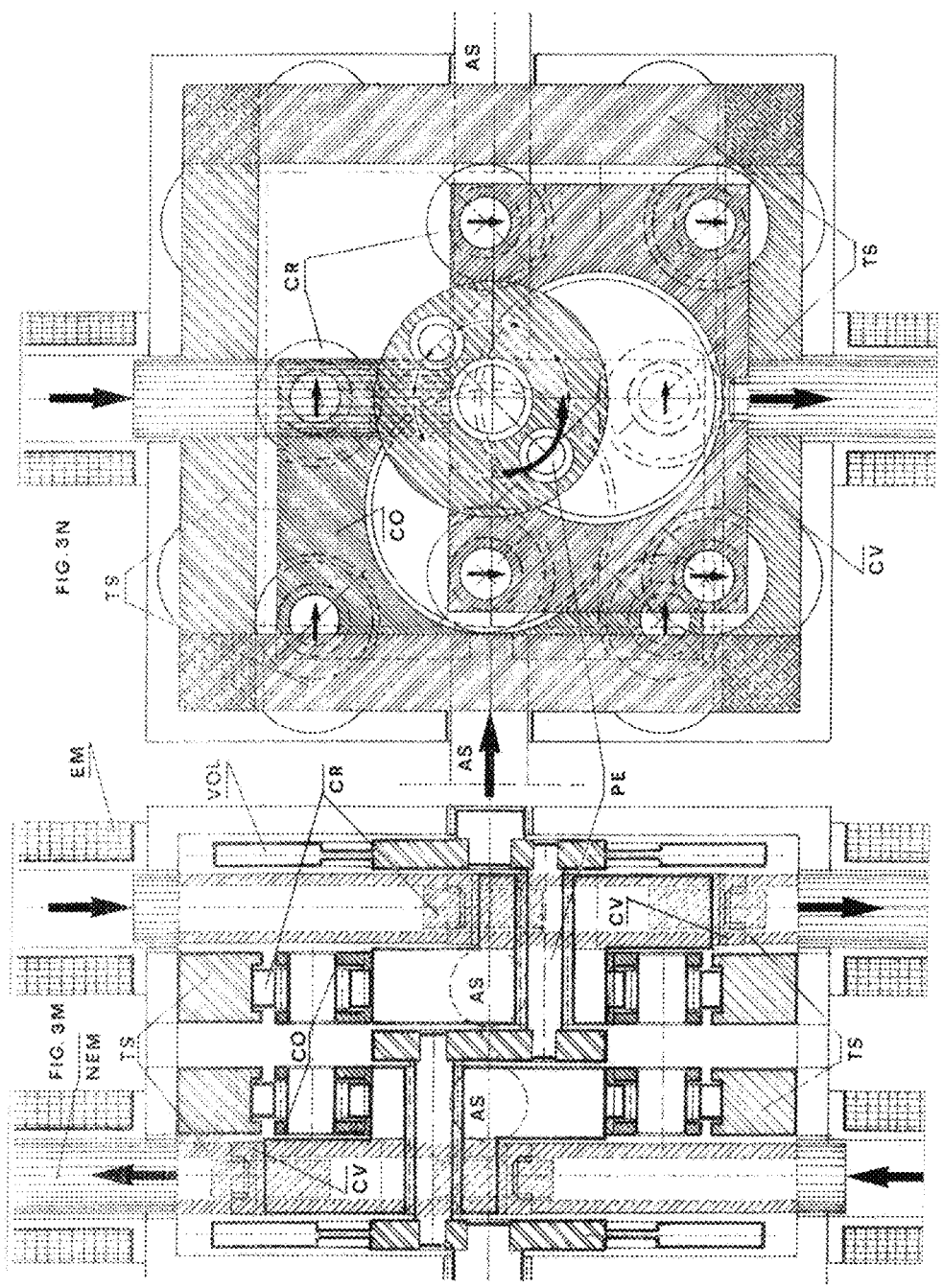

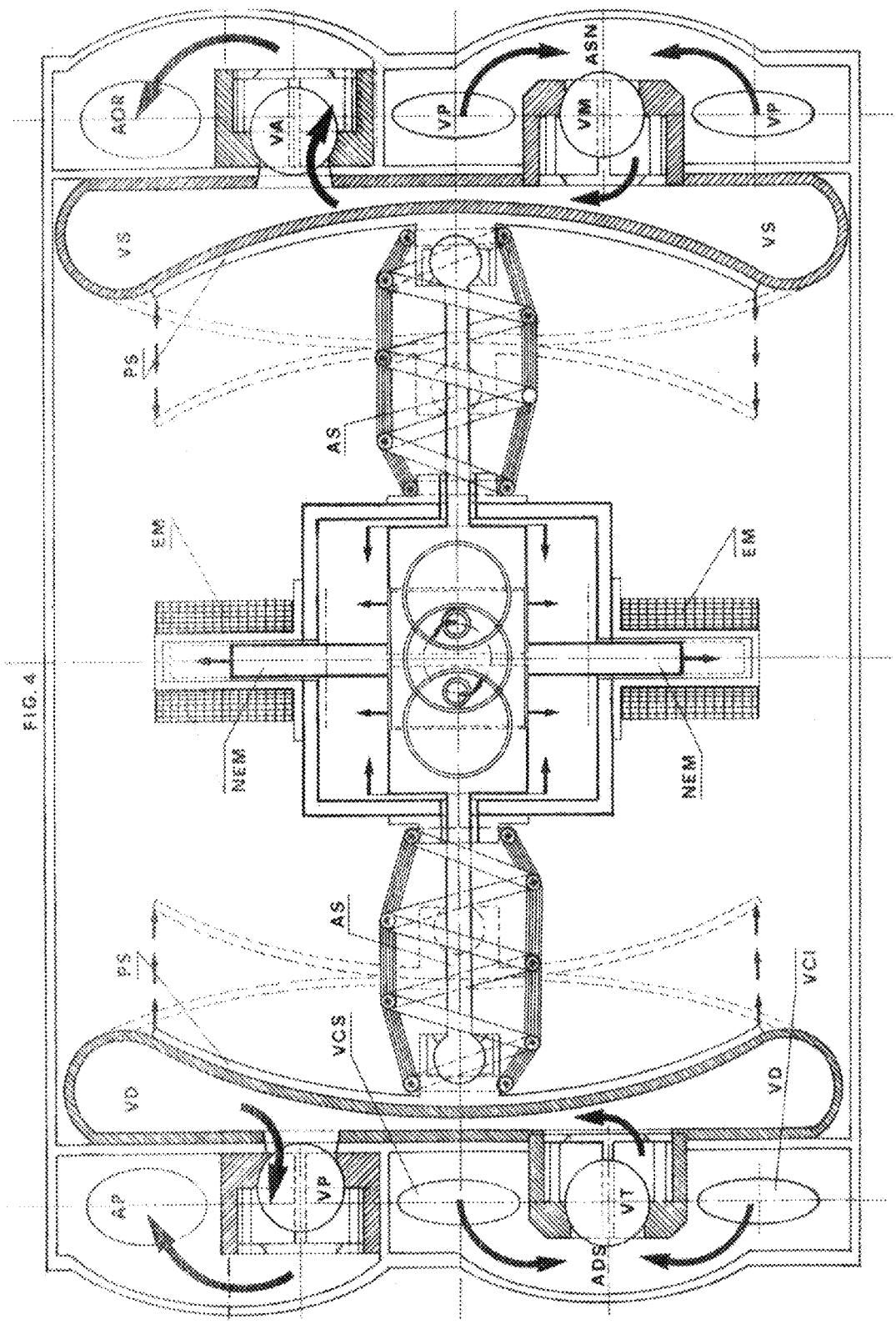

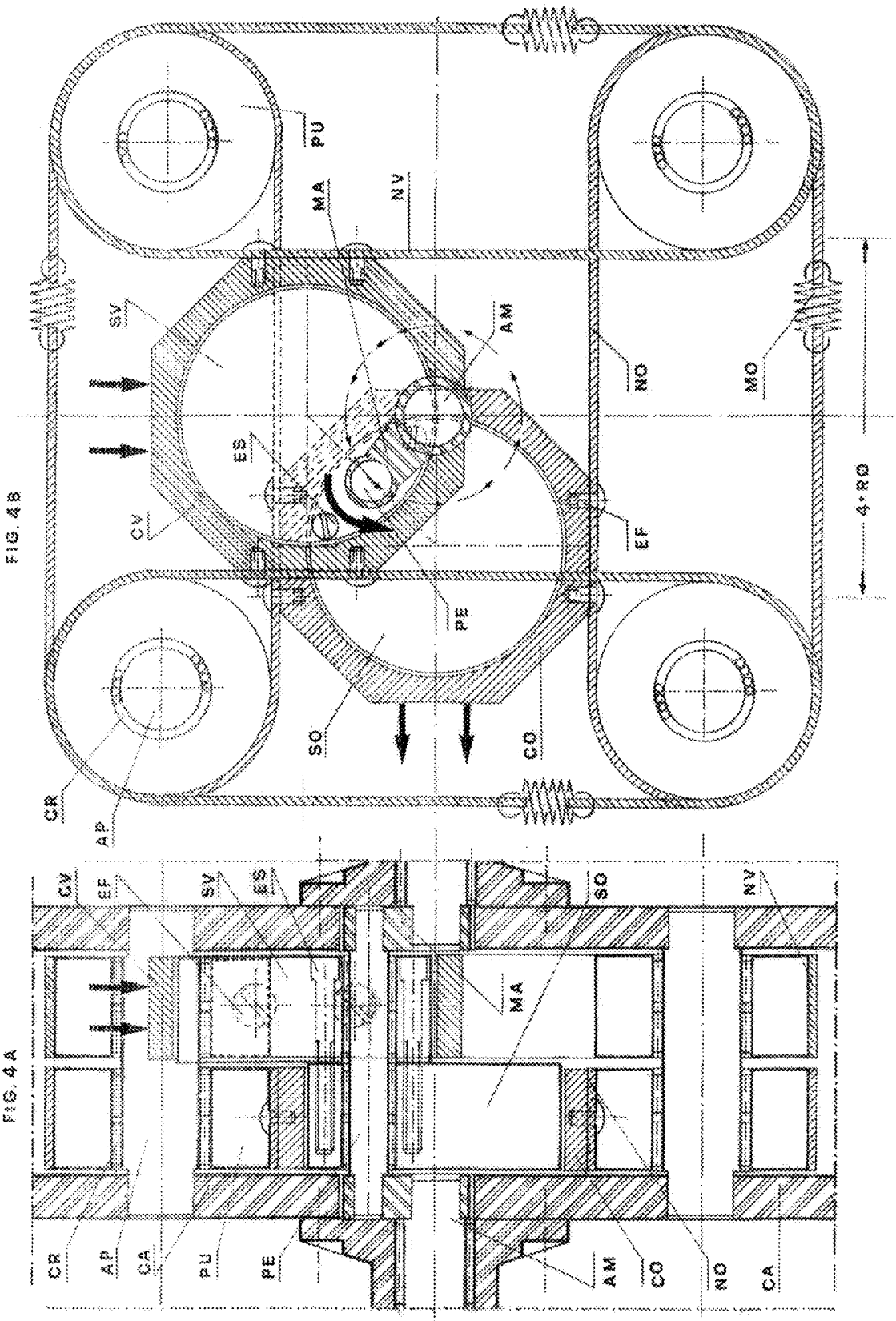

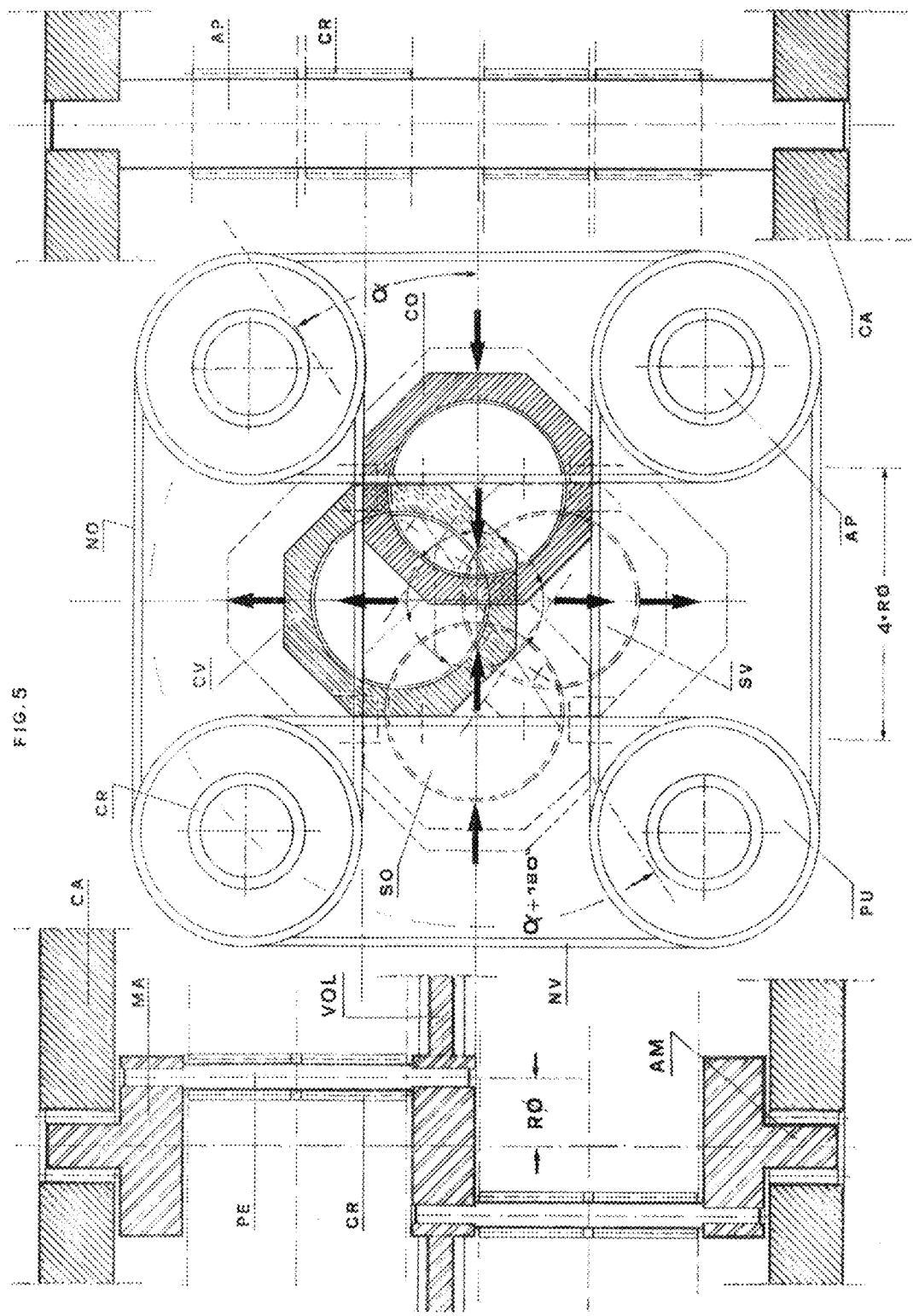

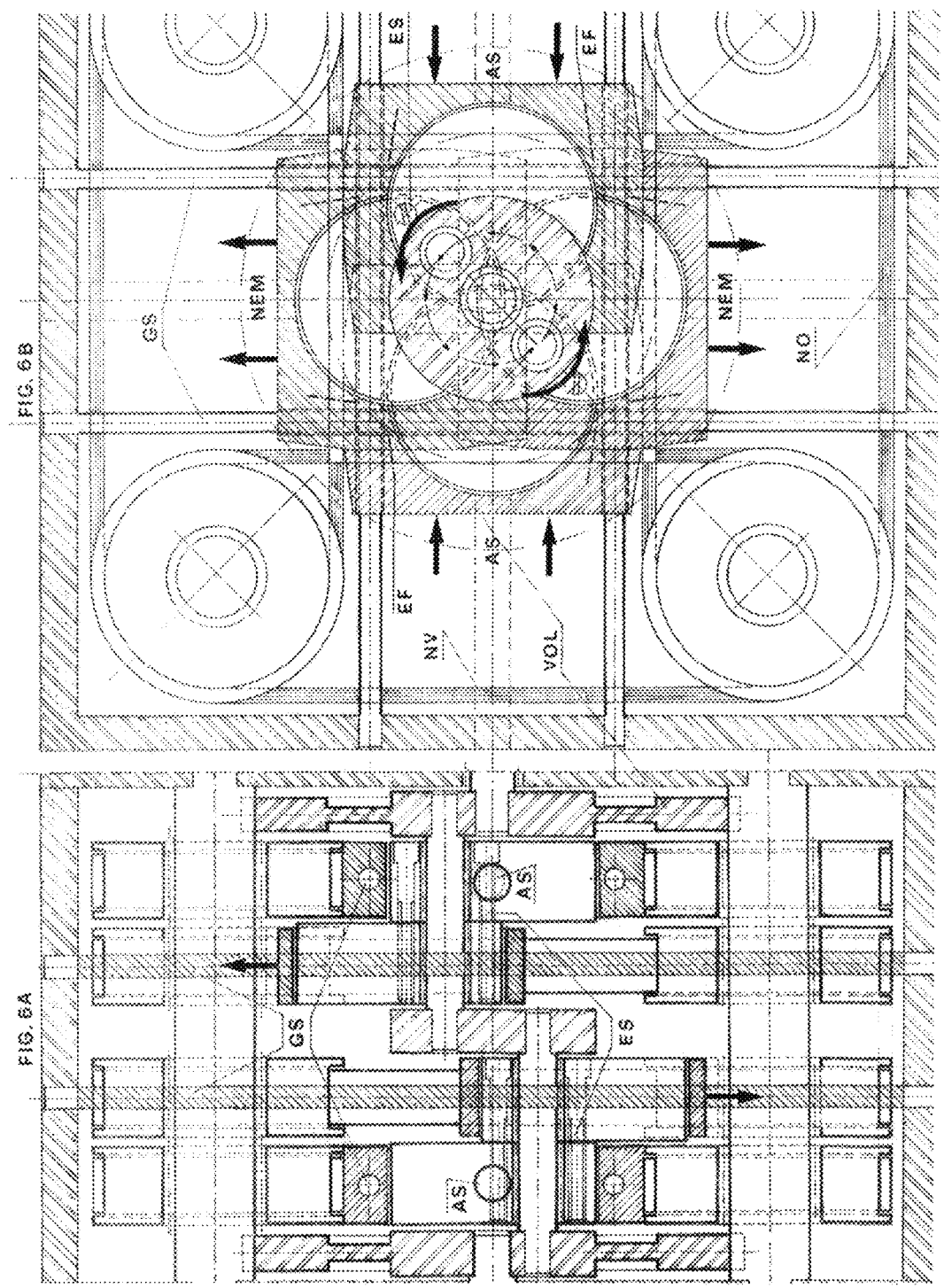

DEVICE FOR GENERATING BILATERAL PRESSURE IMPULSES

SUMMARY OF THE INVENTION

The present invention concerns a device for generating bilateral pressure impulses.

In particular, the present invention concerns an electromechanical device able to manage, through programmed bilateral impulses, the energetic source of operating machines of different kinds, furthermore ensuring a functioning that in technical literature is called "long life", as it is almost wear-free.

Said device finds advantageously application mainly in medicine, in the realization of a permanent artificial heart.

All versions of said electromechanical device, herein below described and shown, are identical as far as the origin of the motion in the respective, reciprocally orthogonal directions is concerned. They differ only according to the progressive research of structural shapes that tend to minimize the shift of the moving parts from said directions, and to reduce the friction between the parts in reciprocal interaction.

The aims of the present invention are reached by means of a device according to the main independent claim 1.

Further features of the present invention are contained in the dependent claims.

The electromechanical device according to the present invention reaches the following important advantages:

- it may be used as a volumetric operator machine that can transfer electric energy transformed in mechanical energy with the highest efficiency towards apparatuses of different typology, that may be mechanically associated to said machine;
- it may be used as a two-stroke propulsion, as it contains pairs of movable units running along reciprocally orthogonal trajectories, and that can each manage correspondent pairs of working chambers, reciprocally aligned and in opposition;
- it comprises a crank mechanism that generates linear trajectories equal to four times the radius of the rotation circumference of said crank mechanism, with an evident increase of the transformed energy amount and/or of any moved fluids;
- it comprises measures for determining the complete elimination of the inertial stresses of the movable units in reciprocating motion;
- it may comprise more than one crank mechanism, placed in correspondence with different portions of the axis of a driving shaft and axially equiangular for obtaining a dynamic balancing, in particular aimed at bench supports;
- it may comprise more than two movable units, each comprising motor discs and sliding guides, axially equiangular with respect to the relative crank mechanism.

As far as the use as a means for managing the energetic source of operating machines of different kinds, and in particular of a permanent artificial heart, the electromechanical device according to the present invention produces the following further advantages:

- it is characterized in reduced encumbrance volumes;
- it is characterized in a perfect structural and functional synthesis between the energy source and the mechanical goals;
- it is nearly completely free of metal parts at non rolling contact;
- it is provided with lubrication in oil bath in closed casing;
- it may be easily associated to processors that may be powered by rechargeable batteries, in charge of managing the frequency and the pressure intensity adequate to the needs of the user, for the lung oxygenation circuits as well as for the circuits of sending into the aorta.

Further characteristics and advantages of the present invention will be more evident from the herein below specification and from the enclosed drawings in which preferred embodiments are shown for exemplifying and not limiting purpose.

BRIEF DESCRIPTION OF THE DRAWINGS

FIGS. 1A and 1B show schematic representations of a first exemplary of a prior art kinematic mechanism.

FIGS. 2A and 2B show schematic representations of a second exemplary of a prior art kinematic mechanism.

FIGS. 3A-3N present schematic representations of exemplary embodiments of the invention.

FIG. 4 presents a summary representation of the invention applied as part of an exemplary mechanism of an artificial heart.

FIGS. 4A-4B present schematic representations of a preferred embodiment of the invention.

FIG. 5 presents another view of a preferred embodiment of the invention.

FIGS. 6A and 6B present additional views of a preferred embodiment of the invention.

BACKGROUND OF THE INVENTION

The writer considers opportune a review of the origin of the motion in the kinematic mechanism which is the basis of the versions of the electromechanical device according to the present invention, by means of schematic representations of the prior art (FIGS. 1 and 2) which illustrate, in two versions, the baseline genesis from which the research aimed at a practical use thereof, started.

It shall be noted that the letters of the figures are accompanied by a second letter "V" or "O", which mean the vertical or horizontal direction of the fix or mobile parts.

In the double axial and radial view of FIG. 1, a main shaft AM jointly supports a crank MA having at its end a pin PE, having a symmetry axis parallel to the one of the main shaft, and to which is axially bound a linear element formed by the solid union of two equal connecting rods BV, BO having their head in common and showing at their feet two pins SV, SO joint to said rods, and forming axial constraint for two cursors CV, CO. The symmetry axis of the pins SV, SO and the one of pin PE are coplanar and parallel. The distance between main shaft AM and pin PE is R$\phi$ and the one between the latter and pins SV, SO also is R$\phi$, while their reciprocal distance is 2*R$\phi$.

In the field of the specific state of the art, document EP 0754 880 A2 describes an improved mechanism for the transformation of rotational motions into harmonic rectilinear motions, comprising in particular two rectilinear guides with coinciding axes, reciprocally orthogonal and traversed by cursors moved in harmonic natural motion by a single pin crank mechanism, consisting of two rods having common head and opposed ends, aligned and connected so as to form a rigid bar carrying on the ends pins axially constrained to said cursors.

Given the disposition shown in FIG. 1 it is known that when shaft AM rotates, supplying cursors CO, CV, axially constrained to the respective pins SV, SO placed at the feet of connecting rods BV, BO, appropriate reciprocally orthogonal sliding guides GS, said cursors move in harmonic natural alternate motion, covering a total rectilinear path of 2*4*Rϕ for each of them and for each round angle of main shaft AM.

The Cartesian coordinates of the axes of pins SV, SO are identified by angle α covered by the longitudinal axis of crank MA which is, as we know, Rϕ:

$$X_o(\alpha) = 2*R\phi*\cos(\alpha);$$

$$Y_o(\alpha) = \phi;$$

$$X_v(\alpha) = \phi;$$

$$Y_v(\alpha) = 2*R\phi*\mathrm{sen}(\alpha).$$

The subscripts "o", "v" of the listed formulas also in this case have the meaning of horizontal and vertical.

It is shown how the crank mechanism, in all its versions, transfers mechanical energy with maximum efficiency, as user of engine torque applied to the main shaft AM as well as like vectors resulting as acting according to linear sliding guides of cursors CV, CO and applied to them, according to the path direction. The present invention uses the second mode by means of traction electromagnets with movable core, as will be described herein below. It is right to anticipate that for describing the motion of the different parts in the figures, the writer has preferred to always start from the generic rotation startup of the main shaft AM instead from impulses of electromagnetic nature coming from the periphery of the device.

Referring now to the geometry of the crank mechanism, it is known that the angle formed by the sliding trajectories of cursors CV, CO is always half the one formed by the plans on which the longitudinal axes of pins SV, SO lie, whereby said plans have the axis of pin PE as their hinge. This explains why in the present case—the axes of the pins SV, SO being coplanar to the one of pin PE, and therefore lying at 180° angles plans—the sliding directions of cursors CV, CO form a 90° angle.

In FIG. 2 we find some functional elements described before, like main shaft AM, crank MA and pin PE; but instead of a double connecting rod BV, BO carrying at its ends pins SV, SO, we find the equivalent of endless bars identical to the one of FIG. 1, and ideally shown by the diameters of the primitive having radius Rϕ of the gear IN, axially constraint to pin PE, rotating inside the toothed ring CD, whose primitive has an obligated diameter of 4*Rϕ.

In the example, two virtual pins SV, SO are arbitrarily chosen, whose longitudinal axes affect the primitive of gear IN at the ends of a virtual bar also chosen among the infinite diameters of the primitive. It is superfluous to note that even in this case the linear module of the real and virtual parts is Rϕ.

Given the disposition shown in FIG. 2 it is known that when main shaft AM rotates, crank MA, through pin PE, forces gear IN to rotate inside toothed ring CD while virtual pins SV, SO—already listed on the preferential diameter—translate of the identical motion already seen on the same trajectories of FIG. 1, no longer benefitting of the constraint of sliding provided by guides GS, but of the sole rotation constraint between toothed ring CD and gear IN.

It is intuitive that the positions of the axes of the virtual pins SV, SO are always found at the angle α covered by the longitudinal axis of crank MA.

DETAILED DESCRIPTION OF THE INVENTION

While describing the seven drawings in which figures from 3A to 3N are shown, the former version—the one comprising gear IN and toothed ring CD inside which it rotates—must be set aside and whose mentioning—as said before—is justified by the heuristic evaluation of the present invention and by its multiple differentiations. By contrast, it is natural to compare FIG. 3B with FIG. 1B, from which it is easy to catch a direct offspring. In fact, there is a main shaft AM, a crank MA, a pin PE, sliding guides GS and cursors CO, CV. The distance 2*Rϕ of the bar or double connecting rod BV, BO, that has become virtual, is shown in dashed lines, while its essential function derives from the assembly of the pair of pins SV, SO, whose axes affect the ends of the dashed segment and whose radius has been increase of an arbitrary measure such as to englobe and to axially constrain pin PE. As said pins SV, SO can not lie on the same plan, they are partially overlapping and reciprocally tightened by means of two fasteners ES that make them an indeformable monoblock. Thus a structural but not functional transformation has been operated, since the pair of increased pins SV, SO, whose axes of symmetry coincide with the corresponding ones in FIG. 1B, in fact assumes the function of the bar, or double connecting rod BV, BO, maintaining the distance of 2*Rϕ.

Given the disposition shown in FIG. 3B it is known that when shaft AM rotates it supplies the cursors CV, CO, that are axially constraint to the respective pins SV, SO, similar and different, not interfering and reciprocally orthogonal sliding guides GS, so that said cursors—overcoming the dead points with the help also of a flywheel VOL shown in FIG. 3A—translate of the same motion seen before, covering the same path.

It can be seen that in FIGS. 3C, 3D embodiments have been performed that do not modify the functionality of the mechanism described in FIGS. 3A, 3B.

With the first embodiment, crank MA is partially shown—in FIG. 3C—as a triple disk and made support besides the flywheel VOL, of a second pin PE having the same structural and functional endowments of the first pin, but diametrically opposed and parallel to it. Such an arrangement of the pins PE makes that during motion the vertically sliding pins SV and the horizontally sliding pins SO are always in reciprocally specular positions with respect to the rotation axis of the main shaft AM, as can be seen in FIG. 3D, along cyclical approaching and subsequent turn away trajectories.

In the second embodiment, the lateral sliding guides GS are replaced with an equal number of honed cylindrical elements, rigidly constrained to carter CA, along which the four cursors CV, CO housing pins SV, SO, may slide with the minimum friction without deviating from the path of belonging.

In FIGS. 3E, 3F the cylindrical sliding guides of the precedent drawing have been replaced with honed bars with rectangular section able to support small rolls CR obtaining de facto linear actuators. The pins SV, SO axially constrained to cursors CV, CO also have been provided with small rolls CR and with this embodiment we can say that all mobile parts of the machine are provided with rolling bearings.

In FIG. 3F, the positions occupied by the cores of electromagnets integral with the cursors vertically moving, as seen by the observer, are anticipated in correspondence to the divergent vertical arrows NEM and that will be shown in the following FIGS. 3G, 3H. In FIG. 3E said positions are one on the prolongation of the other, in a total number of four, equal to the electromagnets who have to transform the electric energy supplied by batteries into the mechanical energy necessary for managing the alternate motion of the cursors.

In FIG. 3F, in correspondence with convergent horizontal arrows AS, the positions taken by stalks of thrust plates are anticipated, integral with the cursors CO, moving horizontally with respect to the observer, and that will be shown in the following FIGS. 3I, 3J. In FIG. 3E, said positions are near the centre, in the middle of the front rectangle of the belonging cursor, in the number of two—one for each side—with the parallel stalks placed at a short distance one from the other.

FIGS. 3G, 3H show the operative structure of the electromagnets EM, highlighting the involvement of the vertical cursors CV to which cores NEM are constrained. It can be noted that these do not interfere with the carter CA, which is provided with passing through holes of appropriate diameter. Electromagnets EM are placed on flanged caps CF which, adhering tightly to carter CA, prevent the lubricant inside to flow out and in the meantime allow the alternate motion of cores NEM, users of air gaps sufficient to exclude passive interferences. The presence of flywheels VOL integral with the main shaft AM helps making the overcoming of the dead points more easy.

The just mentioned flywheels VOL are shown also in FIGS. 3I, 3J in which the involvement of the sole horizontal cursors CO to which stalks AS are in turn constrained to thrust plates PS. Also to this case it applied what has been said about cores NEM of electromagnets EM, i.e. that stalks AS of thrust plates PS shall not interfere with carter CA during motion and shall not allow the lubricant fluid to flow out. To prevent this from happening, armed elastic sleeves MAE are used which, with one end tightened to carter CA and the other one to the belonging plate PS and deforming in the manner of bellows, allow the alternative motion of the respective pressure block, maintaining the mechanism isolated inside.

Going now to FIGS. 3K, 3L, in FIG. 3L, wherein for sake of clarity only pins SV, SO are shown, revolving in cursors CV, CO and associate to pin PE below; a further important variation can be noted which makes the rectilinear trajectory of cursors CV, CO unchangeable overtime, with the reduction practically to null of the deviation from the respective sliding directions. This is obtained replacing the linear actuators, shown in the preceding FIGS. 3E, 3F with an appropriate number of precision roller or ball bearings CR, whereby the inner ring thereof is integral with cold-drawn supports TS shaped in the form of a U, rigidly constrained to carter CA and perfectly aligned and parallel to the sliding directions of cursors CV, CO. The bearings, aligned inside the groove of the supports TS, form a rolling track for the dedicated cursor, with minimal friction.

As shown in the figure, cursors CV, CO cover their own linear trajectory sliding with the minimal friction on the outer rings of bearings CR, whose central axes are parallel and coplanar, maintaining a minimal contact with at least two of them for each active side, and with a maximum number depending from the disposable spaces and from the diametrical dimensions of the same.

It is intuitive that cursors CV, CO with a straight quadrangular profile, need each at least two obligated sliding structures on the opposite sides with minimal difference tolerances.

Passing now to FIGS. 3M, 3N, where in FIG. 3N for the sake of clarity only pins SV, SO are shown revolving in cursors CV, CO associated to pin PE below, a simple variation can be noted that tends to optimize the capacity of the device of maintaining the rectilinear trajectory of cursors CV, CO unvaried, reaffirming zero deviation from the respective sliding directives. This is obtained eliminating the grooves from the sliding supports TS, with the connected bearings CR that are transferred, in a smaller number, with the same functional modes, to the four opposed angles of each cursor CV, CO.

Thus elements TS become rectified bars with rectangular section, with edges of lateral retaining on which vertical cursors CV and horizontal cursors CO slide.

As it is shown in the figure, cursors CV, CO cover their own linear trajectory with the minimal friction, by means of the outer rings of bearings CR axially constrained thereto, on linear bars TS having the function of a track. It is intuitive that cursors CV, CO with a straight quadrangular profile, need each at least two structures TS of obliged sliding on opposite sides, with minimal deviation margins.

FIG. 4 summarizes, in addition to the already explained mechanical part, the main purpose of the present invention, i.e. a scheme for the realization of a permanent artificial heart. Confirming what already explained, in the middle of the figure the device creating the motion is shown, transforming electric energy into mechanical one by exciting the electromagnets EM and causing the alternative vertical motion of the mobile cores NEM. The latter, integral with cursors CV constrained to the central gearing, generate an identical horizontal motion in the thrust plates PS integral with stalks AS connected to the cursors CO of said gearing. The plates PS, during motion, perform a positive pressure followed by a negative one on two casings deformable but inextensible, having the function of the right ventricle VD and of the left ventricle VS. The first casing VD has inside an inlet valve VT (evoking the tricuspid valve) and an outlet valve VP (evoking the pulmonary valve). During the feedback of the corresponding plate, valve VT lets in the right ventricle VD fluid venous blood contained in the right atrium ADS and coming from the upper vena cava VCS and from the lower vena cava VCI, while the pulmonary vein VP remains closed. When the same plate, inverting the sense of the motion, compresses the right ventricular pouch VD, valve VT closes while pulmonary valve VP opens for the passage of blood into the dedicated artery AP. The second casing VS has inside an inlet valve VM (evoking the mitral valve) and an outlet valve VA (evoking the aortic valve). During the feedback of the corresponding plate, valve VM lets oxygenated blood in, contained in the left atrium ASN and coming from the pulmonary veins VP, while the aortic valve VA remains closed. When the same plate, inverting the sense of motion, compresses the left ventricular pouch VS, valve VM closes, while aortic valve VA opens with the passage of blood in the aorta AOR.

Keeping the origin of the motion unvaried, a further embodiment according to the present invention is shown which, according to the author, is considered as a further improvement and therefore proposable.

FIGS. 4A, 4B, 5, 6A, 6B show the latter embodiment, while the illustrative sequence of the contents evokes the one already proposed in the previous specification and drawings, comprising the symbols.

For summarizing with directness the new system of rectilinear guide for cursors CV, CO, FIG. 4A sows one single operative group, as disk cranks MA support one single pin PE, axially constrained to the only monoblock formed by the union of pins SV, SO.

Thus, FIG. 4A shows the proposed embodiment in which the main parts of the device according to the present invention are present, except for the constraints to the sliding present in figures from 3A to 3N, replaced by the combined action of four pairs of pulleys PU, axially constrained to four supporting axes AP, integral with carter CA, forming the support for two inextensible belts NV, sliding vertically, and for as many inextensible belts NO, sliding horizontally, placed in the shape of a ring. In FIG. 4B for each belt NV, NO springs MO are shown: crimping their free flaps, they keep them in tension for reducing to a minimum the deviations from the linear sliding of cursors CV, CO. Pulleys PU, freely rotatable around belonging supporting axis AP, are provided with rolling bearings CR reducing the waste to a minimum. Appropriate fixing element EF ensure the union of belts NV, NO to the respective cursors CV, CO. A perfect analogy exists between the vertically sliding unit and the horizontally sliding unit. Pulleys PU of the one and of the other in fact use the same supporting axes AP, as they are freely rotatable and do not reciprocally interfere.

Given the disposition shown in FIG. 4A, 4B, when shaft AM rotates, supplying cursors CV, CO axially constrained to their respective pins SV, SO, two sliding directions obligated and not interfering one with the other and reciprocally orthogonal, consisting of vertical belts NV and horizontal belts NO, said cursors CV, CO translate of the same motion already observed in the previous versions.

FIG. 5 shows, in the left part, main shaft AM (which shall not be considered to be a perspective view of the central part), with the use of two pins PE having the same functionalities described in the previous embodiments.

The result is shown in the central part of said FIG. 5, where the position of the four cursors CV, CO is defined: two as a function of angle α and, at the same time, the other two as a function of angle α+180°.

To complete FIG. 5 on the right side one of the four supporting axes AP is shown (not to be considered as a perspective view of the central part) on which freely rotate the pulleys, axes AP whose ends are integral with carter CA.

Dashed parts shape the scheme of the position of pulleys PU and of the respective roller bearings CR.

The tension of belts NV, NO is maintained by springs MO, not shown in this figure; this tension—as said before—ensures a minimal deviation from the rectilinear trajectories of cursors CV, CO.

In FIG. 6B, in correspondence with the vertical diverging arrows NEM, the positions occupied by the cores of the electromagnets EM integral with vertical cursors CV are confirmed, while in FIG. 6A said positions are not shown but they are confirmed one on the prolongation of the other, in a total number of four, equal to electromagnets EM who have to transform the electric energy supplied by batteries into the mechanical energy necessary for managing the alternative motion of the cursors.

In FIG. 6B, in correspondence with the converging horizontal arrows AS, the positions occupied by the stalks of the thrust plates PS integral with cursors CO are confirmed, while in FIG. 6A said positions are in the middle of the front rectangle of belonging cursor CO, while the thrust plates are two, one for each side, with parallel stalks AS, placed at a short distance one from the other.

The invention claimed is:

1. A device for generating bilateral pressure impulses, comprising:
   a first operating group including two rectilinear guides (GS) with coinciding centrelines, reciprocally orthogonal and each traversed by a cursor (CV,CO) according to a natural harmonic motion generated by a crank mechanism,
   the crank mechanism having a main shaft (AM), a crank (MA), a single crank pin (PE), two connecting rods (BV, BO) having a common head and opposed feet, aligned and integral for forming a rigid bar, the feet of the two connecting rods (BV, BO) each having an end at which respective pins (SV, SO) are located, each of said pins (SV, SO) axially constrained to a respective cursor (CV, CO), whereby each of said cursors (CV, CO) is distant from an axis of said crank pin (PE) by a measure identical to a measure between an axis of the main shaft (AM) and said crank pin (PE); and
   mobile cores (NEM) of electromagnets (EM), integral with a first cursor (CV) of said cursors (CV, CO) configured to move along a first direction transverse to a second direction of a second cursor (CO) of said cursors (CV, CO), a programmed excitation of said mobile cores (NEM) of electromagnets (EM) configured to supply a mechanical energy for causing an alternating and specular motion of the cursors (CV, CO) for actuating said device.

2. The device according to claim 1, wherein said pins (SV, SO) have an increased radius so as to incorporate, with an axial constraint, the crank pin (PE) of the crank (MA).

3. The device according to claim 1, wherein said pins (SV, SO) are partially and planarly overlapping such to form a functional equivalent of said rigid bar.

4. The device according to claim 1, wherein between said guides of the cursors (CV, CO), axially constrained to pins (SV, SO) and located in different planes, a parallel vertical drop is provided that prevents between said cursors (CV, CO) operating along orthogonal trajectories from interfering with each other.

5. The device according to claim 1, further comprising:
   a second operating group, associated with said main shaft (AM), an axis of a crank pin of the second operating group not aligned, but parallel, to the crank pin of the first operating group, and diametrically opposed to the first operating group with respect to a rotation circumference of an axis of the crank pins (PE),
   wherein said second operative group operatively allows two sliding directions parallel to sliding directions of the first operating group.

6. The device according to claim 1, wherein the alternating and specular motion of the second cursor (CO) of said cursors (CV, CO) exclusively manages thrust plates (PS) for compression and release of deformable and inextensible casings (VD, VS) configured to contain a fluid.

7. The device according to claim 6, wherein said fluid is an incompressible liquid.

8. The device according to claim 6, wherein inside said deformable and inextensible casings (VS, VD), there are inlet valves (VT, VM) and outlet valves (VP, VA) to and from the outside, that allow or not passage of said fluid according to positive or negative pressure created by actuation of the thrust plates (PS).

9. The device according to claim 1, further comprising:
   linear actuators, integral with a housing (CA) of the device and provided in a tightly closed and lubricated environment, for minimizing a deviation of the cursors (CV, CO) from linear trajectories.

10. The device according to claim 1, further comprising:
    outer rings of roller or ball bearings (CR), placed in-line and axially constrained to fixed parallel pins, placed inside bars having a shape of a π and integral with a housing (CA) of the device, forming a dual rolling track for parallel and opposed sides of the cursors (CV, CO), wherein said outer rings are arranged to minimize a deviation of said cursors (CV, CO) from linear trajectories and thereby minimize friction.

11. The device according to claim 1, further comprising:
external rings of roller or ball bearings (CR), placed in-line in grooves on two parallel and opposed sides of each cursor (CV, CO),
wherein said rings are arranged to travel with a minimum friction along respective linear guides, integral with a housing (CA) of the device, and
wherein said rings minimize a deviation of said cursors (CV, CO) from linear trajectories.

12. The device according to claim 1, further comprising:
two pairs of pulleys (PU) axially constrained to pins (AP) integral with a housing (CA) of the device, on which inextensible belts (NV, NO) are mounted, said belts maintained in tension by gripping springs (MO) and constrained at opposite ends of respective cursors (CV, CO) such to follow a linear movement of the respective cursor, for minimizing a deviation of said cursors (CV, CO) from linear trajectories.

13. The device according to claim 12, further comprising:
linear actuators, in addition to said pulleys (PU) and said inextensible belts (NV, NO), configured to further reduce the deviation of the cursors (CV, CO) from the linear trajectories.

14. An operating pulsing machine, comprising a device according to claim 1, configured to operate in two orthogonal moving directions, a first of said moving directions arranged for transforming electric energy into mechanical energy, and a second of said moving directions, operationally related to the first one of said moving directions, is arranged for operating upon a fluid.

15. The device according to claim 2, wherein said pins (SV, SO) are partially and planarly overlapping such to form a functional equivalent of said rigid bar.

16. The device according to claim 7, wherein inside said deformable and inextensible casings (VS, VD), there are inlet valves (VT, VM) and outlet valves (VP, VA) to and from the outside, that allow or not passage of said fluid according to positive or negative pressure created by actuation of the thrust plates (PS).

17. An artificial permanent heart, comprising a device according claim 1.

18. An artificial permanent heart, comprising a device according claim 2.

19. An artificial permanent heart, comprising a device according claim 3.

20. An artificial permanent heart, comprising a device according claim 4.

* * * * *